United States Patent
Ahmed et al.

(10) Patent No.: US 10,384,993 B2
(45) Date of Patent: Aug. 20, 2019

(54) METHOD FOR PRODUCING HYDROCARBONS AND ALCOHOLS

(71) Applicant: SABIC Global Technologies B.V., Bergen op Zoom (NL)

(72) Inventors: Labeeb Chaudhary Ahmed, Riyadh (SA); Khalid Karim, Riyadh (SA); Ali Al-Hammad, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/572,333

(22) PCT Filed: May 5, 2016

(86) PCT No.: PCT/IB2016/052575
§ 371 (c)(1),
(2) Date: Nov. 7, 2017

(87) PCT Pub. No.: WO2016/181265
PCT Pub. Date: Nov. 17, 2016

(65) Prior Publication Data
US 2018/0290953 A1 Oct. 11, 2018

Related U.S. Application Data

(60) Provisional application No. 62/158,699, filed on May 8, 2015.

(51) Int. Cl.
*C07C 29/151* (2006.01)
*C01B 3/36* (2006.01)
(Continued)

(52) U.S. Cl.
CPC .......... *C07C 29/1516* (2013.01); *B01J 4/001* (2013.01); *C01B 3/36* (2013.01); *C01B 3/386* (2013.01);
(Continued)

(58) Field of Classification Search
None
See application file for complete search history.

(56) References Cited

U.S. PATENT DOCUMENTS 4,031,123 A * 6/1977 Espino ............... C07C 29/1512
518/700
4,088,671 A 5/1978 Kobylinski
(Continued)

FOREIGN PATENT DOCUMENTS

EP 1035094 A1 9/2000
EP 2184260 A1 5/2010
(Continued)

OTHER PUBLICATIONS

Jess, A. et al., Fischer-Tropsch-synthesis with Nitrogen-rich Syngas—Fundamentals and Reactor Design Aspects. Appl Catal A: General. 1999; 186(1-2): 321-42.
(Continued)

*Primary Examiner* — Medhanit W Bahta
(74) *Attorney, Agent, or Firm* — Ballard Spahr LLP (57) ABSTRACT

In accordance with the present invention, disclosed herein is a method comprising the steps for producing lower molecular weight C1-C5 hydrocarbons and alcohols. Also disclosed herein, are systems utilized to produce low molecular weight C1-C5 hydrocarbons and alcohols.

18 Claims, 1 Drawing Sheet

(51) Int. Cl.

| | | |
|---|---|---|
| *C07C 1/04* | (2006.01) | |
| *C01B 3/38* | (2006.01) | |
| *C07C 1/24* | (2006.01) | |
| *C10G 2/00* | (2006.01) | |
| *C10G 3/00* | (2006.01) | |
| *B01J 4/00* | (2006.01) | |
| *C07C 29/152* | (2006.01) | |
| *C10L 3/10* | (2006.01) | |

(52) U.S. Cl.
CPC .............. *C07C 1/0485* (2013.01); *C07C 1/24* (2013.01); *C07C 29/152* (2013.01); *C07C 29/1518* (2013.01); *C10G 2/32* (2013.01); *C10G 2/34* (2013.01); *C10G 3/00* (2013.01); *C01B 2203/025* (2013.01); *C01B 2203/0255* (2013.01); *C01B 2203/0261* (2013.01); *C01B 2203/061* (2013.01); *C01B 2203/062* (2013.01); *C01B 2203/1241* (2013.01); *C01B 2203/1258* (2013.01); *C10L 3/103* (2013.01); *C10L 3/105* (2013.01)

(56) References Cited

U.S. PATENT DOCUMENTS

| | | | |
|---|---|---|---|
| 4,207,248 A | 6/1980 | Butter et al. | |
| 5,011,625 A | 4/1991 | Le Blanc | |
| 5,122,299 A | 6/1992 | LeBlanc | |
| 5,362,454 A | 11/1994 | Cizmer et al. | |
| 5,791,161 A | 8/1998 | Manley | |
| 5,852,061 A * | 12/1998 | Alexion | C07C 1/0485 518/700 |
| 6,291,734 B1 | 9/2001 | Stork | |
| 6,444,712 B1 * | 9/2002 | Janda | C01B 3/382 518/700 |
| 6,495,610 B1 | 12/2002 | Brown | |
| 7,220,505 B2 | 5/2007 | Malhotra et al. | |
| 7,554,002 B2 | 6/2009 | Pham Duc | |
| 2005/0020434 A1 | 1/2005 | Ansorge et al. | |
| 2008/0312347 A1 | 12/2008 | Ernst et al. | |
| 2010/0069515 A1 * | 3/2010 | Tirtowidjojo | C07C 1/24 518/705 |
| 2010/0108948 A1 | 5/2010 | Fernie | |
| 2013/0274355 A1 | 10/2013 | Karim et al. | |
| 2014/0135411 A1 | 5/2014 | Karim et al. | |
| 2014/0142206 A1 | 5/2014 | Karim et al. | |

FOREIGN PATENT DOCUMENTS

| | | |
|---|---|---|
| WO | WO-2015/015311 A2 | 2/2015 |
| WO | WO-2016/181266 A1 | 11/2016 |

OTHER PUBLICATIONS

International Search Report and Written Opinion dated Aug. 1, 2016 by the International Searching Authority for Patent Application No. PCT/IB2016/052575, which was filed on May 5, 2016 and published as WO 2016/181265 on Nov. 17, 2016 (Inventor—Ahmed et al.; Applicant—SABIC Global Technologies B.V.)(8 pages).

International Search Report and Written Opinion dated Jul. 7, 2016 by the International Searching Authority for Patent Application No. PCT/IB2016/052576, which was filed on May 5, 2016 and published as WO 2016/181266 on Nov. 17, 2016 (Inventor—Ahmed et al.; Applicant—Sabic Global Technologies B.V.) (11 pages).

* cited by examiner

METHOD FOR PRODUCING HYDROCARBONS AND ALCOHOLS

CROSS-REFERENCE TO RELATED APPLICATIONS

This is a U.S. National Phase Application of International Application No. PCT/IB2016/052575, filed May 5, 2016, which claims the benefit of U.S. Provisional Application No. 62/158,699, filed on May 8, 2015, which are both incorporated herein by reference in their entirety.

BACKGROUND

Syngas (mixtures of $H_2$ and CO) can be readily produced from either coal or methane (natural gas) by methods well known in the art and widely commercially practiced around the world. A number of well-known industrial processes use syngas for producing various oxygenated organic chemicals.

The Fischer-Tropsch catalytic process for catalytically producing hydrocarbons from syngas was initially discovered and developed in the 1920's, and was used in South Africa for many years to produce gasoline range hydrocarbons as automotive fuels. The catalysts typically comprised iron or cobalt supported on alumina or titania, and promoters, like rhenium, zirconium, manganese, and the like were sometimes used with cobalt catalysts, to improve various aspects of catalytic performance. The products were typically gasoline-range hydrocarbon liquids having six or more carbon atoms, along with heavier hydrocarbon products.

Today lower molecular weight C-C5 hydrocarbons (paraffins and/or olefins) are desired and can be obtained from syngas via Fischer-Tropsch catalytic process. There is a need to convert the paraffins and/or olefins obtained into other useful compound(s).

Accordingly, there remains a long-term market need for a new and improved method for producing useful compound(s).

Accordingly, a system and method useful for the production of C-C5 hydrocarbons and alcohols are described herein.

SUMMARY OF THE INVENTION

Disclosed herein is a method comprising the steps of: a) providing natural gas comprising methane and $N_2$; b) removing at least a portion of the $N_2$ from the natural gas, thereby producing a first gas comprising methane and less than about 2 mole % of $N_2$; c) converting at least a portion of the first gas to synthesis gas comprising $H_2$ and CO; d) converting at least a portion of the synthesis gas to a first product stream comprising methane, C2-C9 hydrocarbons, C10+ hydrocarbons, unreacted synthesis gas, and $CO_2$; e) separating at least a portion of the unreacted synthesis gas from the first product stream; and f) converting at least a portion of the unreacted synthesis gas to a first product comprising methanol and C2+ alcohols.

Also disclosed herein is a system comprising a) a gas expander comprising a first inlet and a first outlet; and b) an alcohol reactor comprising a second inlet and a second outlet, wherein the gas expander is in fluid communication with the alcohol reactor via a first connector, wherein the first connector is connected to the first outlet of the gas expander and the first inlet of the alcohol reactor.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive of the invention, as claimed.

DESCRIPTION OF THE FIGURES

The accompanying figures, which are incorporated in and constitute a part of this specification, illustrate several aspects, and together with the description, serve to explain the principles of the invention.

DETAILED DESCRIPTION

The present invention can be understood more readily by reference to the following detailed description of the invention.

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

All publications mentioned herein are incorporated herein by reference to disclose and describe the methods and/or materials in connection with which the publications are cited.

1. Definitions

In this specification and in the claims which follow, reference will be made to a number of terms which shall be defined to have the following meanings:

As used in the specification and in the claims, the term "comprising" can include the aspects "consisting of" and "consisting essentially of" Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a hydrocarbon" includes mixtures of two or more hydrocarbons.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The terms "first," "first gas," "first product stream," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent ("wt %") of a component, unless specifically stated to the contrary, is based on the total weight of the formulation or composition in which the component is included. For example, if a particular element or component in a composition or article is said to have about 80% by weight, it is understood that this percentage is relative to a total compositional percentage of 100% by weight.

A mole percent ("mole %") of a component, unless specifically stated to the contrary, is based on the total number of moles of all chemical components present in the formulation or composition in which the component is included. For example, if a particular element or component in a composition is said to be present in amount about 1 mole %, it is understood that this percentage is relative to a total compositional percentage of 100% by mole.

As used herein, the terms "syngas" or "synthesis gas" are used interchangeably herein.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

2. Fisher-Tropsch Catalytic Process

The Fischer-Tropsch catalytic process for producing hydrocarbons from syngas is known in the art. Several reactions can take place in a Fischer-Tropsch process, such as, a Fischer-Tropsch (FT) reaction, a water gas shift reaction, and a hydrogen methanation, as shown in Scheme 1.

FT reaction: n CO+2nH$_2$→(CH$_2$)$_n$+H$_2$O

Water Gas Shift Reaction (WGS): CO+H$_2$O→CO$_2$+H$_2$

Methanation CO+H$_2$→CH$_4$+H$_2$O    Scheme 1

The gases that are being mixed in the Fischer-Tropsch process described herein comprise H$_2$ and CO. The H$_2$/CO molar ratio of the feed can be from about 0.5 to about 4. For example, the H$_2$/CO molar ratio can be from about 1.0 to about 3.0, such as, for example, from about 1.5 to about 3.0, or in another example, from about 1.5 to about 2.5. It will be appreciated that the H$_2$/CO molar ratio can control the selectivity of the hydrocarbons that are being produced. The consumption molar ratio of H$_2$/CO is usually from about 1.0 to about 2.5, such as for example, from about 1.5 to 2.1. This ratio increases as long as the water gas shift reaction is active, and thus, the use of a feed ratio below the consumption ratio will result in a stable H$_2$/CO ratio during the reaction within an acceptable range (normally below about 2). The H$_2$ and CO are catalytically reacted in a Fischer-Tropsch reaction.

A Fischer-Tropsch process that targets the production of light olefins (C2-C6 olefins) is desired and such process can produce a significant amount of C2-C3 hydrocarbons comprising C2-C3 olefins and C2-C3 paraffins. As disclosed herein, unreacted syngas from a Fischer-Tropsch process can be further converted to a first alcohol product comprising methanol and C2+ alcohols.

3. System

Disclosed herein is a system comprising: a) a gas expander comprising a first inlet and a first outlet; and b) an alcohol reactor comprising a second inlet and a second outlet, wherein the gas expander is in fluid communication with the alcohol reactor via a first connector, wherein the first connector is connected to the first outlet of the gas expander and the first inlet of the alcohol reactor.

Gas expanders are known in the art. A gas expander can, for example, be a turboexpander. A gas expander expands high pressured gas to produce work. Because work is extracted from the expanding high pressure gas, the expansion is approximated by an isentropic process (i.e., a constant entropy process) and the lower pressure exhaust gas from the gas expander is at a low temperature, such as, for example, a temperature from about −90° C. to about −160° C. Methane has a boiling point of −161.5° C. Ethane has a boiling point of −88.6° C. C3+ hydrocarbons have higher boiling points than ethane. Thus, at a temperature from —90° C. to about −160° C. methane is in gas phase while C2+ hydrocarbons are in liquid phase. At such conditions methane can be separated from C2+ hydrocarbons. In one aspect, the gas expander can be in fluid communication with a refrigeration unit, such as, for example, a cold box, to provide further cooling for the separation process of methane from C2+ hydrocarbons.

The alcohol reactor is any vessel capable of being effective for producing alcohol, such as methanol, ethanol, propanol, butanol, and/or pentanol, from syngas, such as from unreacted syngas. The alcohol reactor can be a single vessel or a plurality of vessels. The alcohol reactor contains at least one catalyst composition that can catalyze the conversion of syngas into alcohols. For example, the alcohol reactor can comprise one or more tubes filled with one or more catalysts.

The alcohol reactor for converting syngas into alcohols can be engineered and operated in a wide variety of ways. The reactor operation can be continuous, semi-continuous, or in batch.

Any suitable catalyst or combination of catalysts can be used in a reactor to catalyze reactions converting syngas to alcohols. Suitable catalysts include, but are not limited to, $ZnO/Cr_2O_3$, $Cu/ZnO$, $Cu/ZnO/Al_2O_3$, $Cu/ZnO/Cr_2O_3$, $Cu/ThO_2$, Co/Mo/S, Co/S, Mo/S, Ni/S, Ni/Mo/S, Ni/Co/Mo/S, Rh, Ti, Fe, Ir, and any of the foregoing in combination with Mn and/or V. The addition of basic promoters, for example, K, Li, Na, K, Rb, and Cs, can increase the activity and selectivity of some of these catalysts for the production of alcohols. Basic promoters include alkaline-earth and rare-earth metals. Non-metallic bases can also serve as effective promoters in some embodiments. The catalyst can be selected to minimize the formation of $CO_2$ and $CH_4$ under reaction conditions. Certain catalysts that can be used include Co—Mo—S materials promoted with potassium.

In one aspect, the system further comprises a Fischer-Tropsch reactor comprising a third inlet and a third outlet, wherein the Fischer-Tropsch reactor is in fluid communication with the gas expander. The Fischer-Tropsch reactor and the gas expander can be in fluid communication via one or more units that are capable of removing $CO_2$ and/or wax from a product comprising methane, C2-C9 hydrocarbons, C10+ hydrocarbons, aromatics, unreacted synthesis gas, wax, and $CO_2$.

For example, the one or more units that are capable of removing $CO_2$ comprise a $CO_2$ separating membrane. In another example, the one or more units that are capable of removing wax can comprise a temperature control with allows the product to be cooled to a temperature below the melting point of the wax, thereby solidifying the wax. Subsequent cooling steps can be performed to separate the aqueous phase from the gas phase. The second cooling step can be followed by another cooling step, wherein the organic phase is separated from the gas phase.

Isothermal and/or adiabatic fixed bed reactors can be used as a Fischer-Tropsch reactor, which can carry out the Fischer-Tropsch process. The isothermal and/or adiabatic fixed bed reactors are used to convert syngas to hydrocarbon products, including, olefins, paraffins, and alcohols.

The Fischer-Tropsch reactor can comprise one or more Fischer-Tropsch catalysts. Fischer-Tropsch catalysts are known in the art and can, for example, be Fe based catalysts and/or Co based catalysts and/or Ru based catalysts. Such catalysts are described in U.S. Pat. Nos. 4,088,671 and 4,207,248, which are incorporated herein by their entirety, specifically for their disclosure regarding Fischer-Tropsch catalysts.

In one aspect, the system further comprises a partial oxidation reactor comprising a fourth inlet and a fourth outlet, wherein the partial oxidation reactor is in fluid communication with the Fischer-Tropsch reactor. The partial oxidation reactor can be in fluid communication with the Fischer-Tropsch reactor via a second connector. The second connector can be connected to the fourth outlet of the partial oxidation reactor and to the third inlet of the Fischer-Tropsch reactor.

In one aspect, the partial oxidation reactor comprises a thermal partial oxidation reactor and a catalytic partial oxidation reactor. In one aspect, the partial oxidation reactor is a thermal partial oxidation reactor. In yet another aspect, the partial oxidation reactor is a catalytic partial oxidation reactor. As one of ordinary skill in the art would readily appreciate, if the partial oxidation reactor used to convert at least a portion of the first gas to synthesis gas is a catalytic partial oxidation reactor, it is preferable that the first gas comprises less than about 1,000 ppm, less than about 800 ppm, less than about 600 ppm, less than about 400 ppm, less than about 200 ppm, less than about 100 ppm, or less than about 50 ppm of sulfur, or less than 25 ppm of sulfur.

A partial oxidation reactor is any vessel capable of being effective for producing syngas from a mixture of methane and oxygen. The production of syngas can be caused by a reaction between methane and oxygen, which can take place in the presence of any suitable partial oxidation catalyst. Other carbon containing materials, such as C2+ hydrocarbons, can also be reacted with oxygen to produce syngas. The partial oxidation reactor is configured to be operated at a gas pressure greater than 1 atmosphere (>100 kPa), such as above 2 atmospheres, which is advantageous for optimizing syngas production space-time yields. The partial oxidation reactor can comprise a fixed bed comprising the partial oxidation catalyst.

For example, the methane in the natural gas can be preheated to about 30° C.-750° C. before mixing with the oxygen. The gas mixture then passes over the catalyst to the point at which the partial oxidation reaction initiates.

The net partial oxidation reaction conditions can promoted by optimizing the concentrations of methane and oxygen, such as a molar ratio in the range of from about 1.5:1 to about 3.3:1 $C:O_2$.

In one aspect, the first gas disclosed herein comprises is at least about 80 wt % methane, at least about 90 wt % of methane, or at least about 95 wt % methane. In yet another aspect, the first gas comprises from about 80 wt % to about 99 wt % of methane.

In one aspect, the system further comprises an $N_2$ removal unit comprising a fifth inlet and a fifth outlet, wherein the partial oxidation reactor is in fluid communication with the partial oxidation reactor. The $N_2$ removal unit can be in fluid communication with the partial oxidation reactor via a third connector. The third connector can be connected to the fifth outlet of the $N_2$ removal unit and to the fourth inlet of the partial oxidation reactor.

The $N_2$ removal unit can be configured to in a number of ways to remove $N_2$ from natural gas. In one aspect, the $N_2$ removal unit can comprise a membrane that separates at least a portion of the $N_2$ from natural gas. In another aspect, the $N_2$ removal unit can be configured for cryogenic processing. Methane has a boiling point of −161.5° C. $N_2$ has a boiling point of −195.7° C. Compression and distillation columns drastically reduces the temperature of the gas mixture to a point where methane is liquefied and the $N_2$ is not. In yet another aspect, the $N_2$ removal unit can comprise a pressure swing adsorption unit or lean oil absorption unit. In a yet further aspect, the $N_2$ can be removed by utilizing nitrogen binding complexes.

In one aspect, the system further comprises a deethanizer comprising a sixth inlet and a sixth outlet and/or a depropanizer comprising a seventh inlet and a seventh outlet, wherein the gas expander and the alcohol reactor are in fluid communication with the deethanizer and/or depropanizer. In one aspect, the system further comprises a deethanizer. In another aspect, the system further comprises a depropanizer. The deethanizer and/or depropanizer can be in fluid communication with the gas expander via a fourth connector. The fourth connector can be connected to the sixth inlet of the deethanizer and/or the seventh inlet of the depropanizer and to a ninth outlet of the gas expander. The fourth connector can be connected to the sixth inlet of the deethanizer and/or the seventh inlet of the depropanizer and to a tenth outlet of the alcohol reactor.

A deethanizer is known in the art. A deethanizer separates C2 hydrocarbons, disclosed herein, from other hydrocarbons, such as C3-C9 and C10+ hydrocarbons. A deethanizer can be a fractionation column, which uses distillation separation technologies for hydrocarbon separation. Dethanizers are, for example, described in U.S. Pat. No. 7,554,002, European Patent 1035094, and U.S. Pat. No. 5,791,161, which are incorporated herein by their entirety, specifically for their disclosure regarding deethanizers.

A depropanizer is known in the art. A depropanizer separates C3 hydrocarbons, disclosed herein, from other hydrocarbons, such as C2, C4-C9, and C10+ hydrocarbons. A depropanizer can be a fractionation column, which uses distillation separation technologies for hydrocarbon separation. Depropanizers are, for example, described in U.S. Pat. No. 6,291,734, which is incorporated herein by its entirety, specifically for its disclosure regarding depropanizer.

In one aspect, the system further comprises an olefin separator comprising an eighth inlet and an eight outlet, wherein the olefin separator is in fluid communication with the deethanizer and/or depropanizer. The olefin separator can be in fluid communication with the deethanizer and/or depropanizer via a fifth connector. The fifth connector can be connected to the sixth outlet of the deethanizer and/or the seventh outlet of the depropanizer and to an eighth inlet of the olefin separator.

An olefin separator is a separator that can separate olefins from paraffins and other products. The olefin separator can be a separator that cryogenically can separate olefins from paraffins. For example, the olefin separator can separate ethylene and propylene from a hydrocarbon stream. Olefin separators are known in the art and can also include distillation and membrane separation, or a combination thereof.

In one aspect, the system further comprises a sulfur removal unit comprising an eleventh inlet and a eleventh outlet, wherein the sulfur removal unit is in fluid communication with the $N_2$ removal unit. The sulfur removal unit can be in fluid communication with the $N_2$ removal unit via a sixth connector. The sixth connector can be connected to the eleventh outlet of the sulfur removal unit and to the fifth inlet of the $N_2$ removal unit.

In certain aspects, sulfur can be removed from natural gas by any methods known in the art. For example, sulfur is removed from natural gas by a process of hydrodesulphurization. For example, sulfur can be removed by the hydrodesulphurization at a temperature in the range from about 300 to 400° C. and a pressure in the range from about 30 to about 130 atmospheres, in the presence of a catalyst comprising an alumina base impregnated with active metals. In some aspects, the active metals can comprise cobalt, molybdenum or a combination thereof. In other aspects, the active metals can further comprise nickel, or a combination of nickel and molybdenum. The organic sulfur can be converted to $SH_2$, which can subsequently be removed using a ZnO type catalyst bed.

Optionally, in various aspects, the disclosed system can be operated or configured on an industrial scale. In one aspect, the reactors described herein can each be an industrial size reactor. For example, the gas expander can be an industrial size reactor. In another example, the alcohol reactor can be an industrial size reactor. In yet another example, the Fischer-Tropsch reactor can be an industrial size reactor. In yet another example, the partial oxidation reactor can be an industrial size reactor. In yet another example, the $N_2$ removal unit can be an industrial size reactor. In yet another example, the deethanizer can be an industrial size reactor. In yet another example, the depropanizer can be an industrial size reactor. In yet another example, the olefin separator can be an industrial size reactor. In yet another example, the sulfur removal unit can be an industrial size reactor.

The reactors, units, and vessels disclosed herein can have a volume of at least about 1,000 liters, about 2,000 liters, about 5,000 liters, or about 20,000 liters. For example, the reactor can have a volume from about 1,000 liter to about 20,000 liters.

In one aspect, the gas expander can have a volume of at least about 1,000 liters, about 2,000 liters, about 5,000 liters, or about 20,000 liters. For example, gas expander can have a volume from about 1,000 liter to about 20,000 liters.

In one aspect, the alcohol reactor can have a volume of at least about 1,000 liters, about 2,000 liters, about 5,000 liters, or about 20,000 liters. For example, alcohol reactor can have a volume from about 1,000 liter to about 20,000 liters.

In one aspect, the Fischer-Tropsch reactor can have a volume of at least about 1,000 liters, about 2,000 liters, about 5,000 liters, or about 20,000 liters. For example, the Fischer-Tropsch reactor can have a volume from about 1,000 liter to about 20,000 liters.

In one aspect, the partial oxidation reactor can have a volume of at least about 1,000 liters, about 2,000 liters, about 5,000 liters, or about 20,000 liters. For example, the partial oxidation reactor can have a volume from about 1,000 liter to about 20,000 liters.

In one aspect, the $N_2$ removal unit can have a volume of at least about 1,000 liters, about 2,000 liters, about 5,000 liters, or about 20,000 liters. For example, the $N_2$ removal unit can have a volume from 1,000 liter to 20,000 liters.

In one aspect, the deethanizer can have a volume of at least about 1,000 liters, about 2,000 liters, about 5,000 liters, or about 20,000 liters. For example, the deethanizer can have a volume from about 1,000 liter to about 20,000 liters.

In one aspect, the depropanizer can have a volume of at least about 1,000 liters, about 2,000 liters, about 5,000 liters, or about 20,000 liters. For example, the depropanizer can have a volume from about 1,000 liter to about 20,000 liters.

In one aspect, the olefin separator can have a volume of at least about 1,000 liters, about 2,000 liters, about 5,000 liters, or about 20,000 liters. For example, the olefin separator can have a volume from about 1,000 liter to about 20,000 liters.

In one aspect, the sulfur removal unit can have a volume of at least about 1,000 liters, about 2,000 liters, about 5,000 liters, or about 0,000 liters. For example, the sulfur removal unit can have a volume from about 1,000 liter to about 20,000 liters.

In one aspect, the syngas production reactor can have a volume of at least about 1,000 liters, about 2,000 liters, about 5,000 liters, or about 20,000 liters. For example, the syngas production reactor can have a volume from about 1,000 liter to about 20,000 liters.

Figure 1:
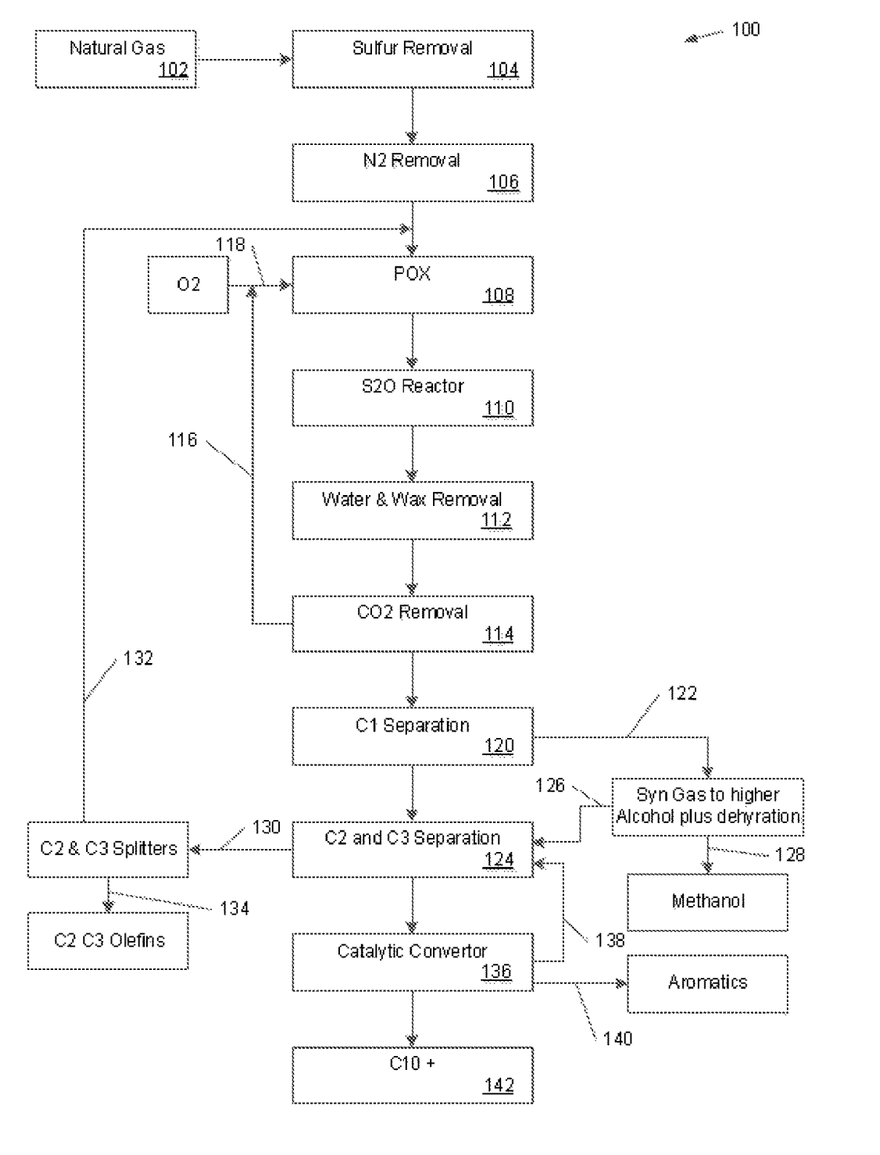
The Figure shows a flow diagram of a system and a method described herein.

Now referring to the Figure, which shows a non-limiting exemplary aspect of the system and method disclosed herein. The Figure shows a system (100). The system has a natural gas providing unit (102). The natural gas providing unit is in fluid communication with a sulfur removal unit (104). The sulfur removal unit is in fluid communication with $N_2$ removal unit (106). The $N_2$ removal unit is in fluid communication with a partial oxidation reactor (POX) (108), wherein syngas is produced. The partial oxidation reactor (108) is in fluid communication with a Fischer-Tropsch reactor ("a syngas to olefin reactor" or S2O unit) (110). The Fischer-Tropsch reactor (110) is in further fluid communication with a wax and water removal unit (112). The wax and water removal unit is in further fluid communication with $CO_2$ removal unit (114). The $CO_2$ removal unit is in fluid communication with methane separation unit (120). The $CO_2$ removal unit is separately further connected by fluid communication (116) with an $O_2$ supply unit. The $O_2$ supply unit is in further fluid communication (118) with a partial oxidation reactor (POX) (108). The methane separation unit is in fluid communication with a C2 and C3 separation unit (124). The methane separation unit is also separately in fluid communication (122) with an alcohol conversion and dehydration unit. The alcohol dehydration unit is in fluid communication (128) with a methanol separation unit. The alcohol dehydration unit is also in fluid communication (126) with the C2 and C3 separation unit (124). The C2 and C3 separation unit is in fluid communication (130) with C2 and C3 splitters. The C2 and C3 splitters are in fluid communication (132) with the partial oxidation reactor (108) and separately in further fluid communication with a C2 and C3 olefin separation unit (134). The C2 and C3 separation unit (124) is in further fluid communication with a catalytic conversion unit (136). The catalytic conversion unit (136) is in fluid communication (138) with the C2 and C3 separation unit (124). The catalytic conversion unit is also in fluid communication (140) with an aromatics separation unit and a C10+ separation unit (142).

4. Methods

Also disclosed herein is a method of producing a first alcohol product comprising methanol and C2+ alcohols.

Disclosed herein is a method comprising the steps of: a) providing natural gas comprising methane and $N_2$; b) removing at least a portion of the $N_2$ from the natural gas, thereby producing a first gas comprising methane and less than about 2 mole % of $N_2$; c) converting at least a portion of the first gas to synthesis gas comprising $H_2$ and CO; d) converting at least a portion of the synthesis gas to a first product stream comprising methane, C2-C9 hydrocarbons, C10+ hydrocarbons, unreacted synthesis gas, and $CO_2$; e) separating at least a portion of the unreacted synthesis gas from the first product stream; and f) converting at least a portion of the unreacted synthesis gas to a first alcohol product comprising methanol and C2+ alcohols.

By converting unreacted synthesis gas to a first alcohol product, a lower amount of Fischer-Tropsch reactors can be used, which is cost effective.

Natural gas comprising methane and nitrogen ($N_2$) is provided (102). At least a portion of the $N_2$ from the natural gas is removed to produce a first gas comprising methane and less than about 2 mole % of $N_2$ utilizing the nitrogen removal unit (106). In one aspect, the nitrogen removal can be done utilizing any nitrogen removal units described herein. In one aspect, the first gas can comprise less than about 1.5 mole % of $N_2$. For example, the first gas comprises less than about 0.5 mole % of $N_2$. In yet another example, the first gas comprises less than about 0.3 mole % of $N_2$. In a yet further example, the first gas comprises less than about 0.1 mole % of $N_2$.

In some aspects, the natural gas can further comprise sulfur. In one aspect, the method disclosed herein can further comprise the step of removing at least a portion of the sulfur from the natural gas utilizing the sulfur removal unit (104). In certain aspects, an amount of sulfur left in the natural gas after the step of removal is less than about 1,000 ppm, less than about 800 ppm, less than about 600 ppm, less than about 400 ppm, less than about 200 ppm, less than about 100 ppm, or less than about 50 ppm, or less than 25 ppm of sulfur.

In one aspect, the step of converting at least a portion of the first gas to synthesis gas comprising $H_2$ and CO is performed in the partial oxidation reactor (108).

In another aspect, if the thermal partial oxidation reactor is used to convert the first gas to synthesis gas, the conversion can occur at a temperature in the range from about 1,200° C. to about 2,000° C., including exemplary values of about 1,200° C., about 1,400° C., about 1,600° C., about 1,800° C., or 2,000° C. In another aspect, if the catalytic partial oxidation reactor is used to convert the first gas to synthesis gas, the conversion occurs at a temperature in the range from about 700° C. to about 1,000° C., including exemplary values of about 750° C., about 800° C., about 850° C., about 900° C., and about 950° C.

In another aspect, at least about 80 wt % of the first gas is converted to the synthesis gas comprising $H_2$ and CO, including exemplary values of at least about 85 wt %, at least about 90 wt %, and at least about 95 wt %. In yet another aspect, from about 80 wt % to about 99 wt %, such as from about 80 wt % to about 90 wt %, of the first gas is converted to the synthesis gas.

In a further aspect, at least a portion of the formed synthesis gas is converted in the Fisher-Tropsch reactor (110) to a first product stream comprising methane, C2-C9 hydrocarbons, C10+ hydrocarbons, unreacted synthesis gas, and $CO_2$.

In one aspect, the C10+ hydrocarbons can comprise C10-C50 hydrocarbons. In a further aspect, the C10+ hydrocarbons can comprise C10-C30 hydrocarbons. In a yet further aspect, the C10+ hydrocarbons can comprise C10-C20 hydrocarbons. In one aspect, the C10+ hydrocarbons can comprise olefins and paraffins. For example, the C10+ hydrocarbons can comprise C10-C30 olefins and paraffins, or C10-C20 olefins and paraffins. In one aspect, the C2+ alcohols comprise any C2-C50 alcohols. In another aspect, the C2+ alcohols can comprise C2-C30 alcohols. In a further aspect, the C2+ alcohols can comprise C2-C20 alcohols. It is understood that the C2+ alcohols comprise primary alcohols, secondary alcohols, or tertiary alcohols, or any combination thereof.

In one aspect, the C2-C9 hydrocarbons in the first product stream comprise C2-C5 hydrocarbons. In one aspect, the first product stream comprises at least about 5 wt %, at least about 10 wt %, at least about 15 wt %, at least about 20 wt %, at least about 25 wt %, at least about 30 wt %, at least about 40 wt %, or at least about 60 wt % of C2-C5 hydrocarbons. In yet another aspect, the first product stream comprises from about 5 wt % to about 99 wt % of C2-C5 hydrocarbons. It is understood that C2-C5 hydrocarbons can comprise olefins and paraffins.

In one aspect, the first product stream comprises from about 20 wt % to about 70 wt % of C2-C5 hydrocarbons. In yet another aspect, the first product stream comprises from about 20 wt % to about 70 wt % of C2-C5 olefins and paraffins. In a yet further aspect, the first product stream comprises from about 20 wt % to about 70 wt % of C2-C5 olefins.

In one aspect, the first product stream comprises from about 5 wt % to about 30 wt % of C2-C3 hydrocarbons. In another aspect, C2-C3 hydrocarbons comprise C2-C3 olefins and C2-C3 paraffins. In yet another aspect, the first product stream comprises from about 5 wt % to about 30 wt % of C2-C3 olefins and C2-C3 paraffins. In a yet further aspect, the first product stream comprises from about 5 wt % to about 20 wt % of C2-C3 olefins and C2-C3 paraffins. In yet another aspect, the first product stream comprises from about 5 wt % to about 15 wt % of C2-C3 olefins and C2-C3 paraffins.

In some aspects, the first product stream comprises from about 5 wt % to about 30 wt % of C2-C3 olefins. In yet other aspects, the first product stream comprises from about 5 wt % to about 20 wt % of C2-C3 olefins. In further aspects, the first product stream comprises from about 5 wt % to about 15 wt % of C2-C3 olefins.

During the conversion step of the at least a portion of the synthesis gas to the first product stream, $CO_2$ can be formed as a reaction by-product. In one aspect, the method disclosed herein further comprises a step of separating $CO_2$ from the first product stream. In one aspect, $CO_2$ can be separated from the first product stream using the systems described herein. In yet another aspect, $CO_2$ can be separated from the first product stream utilizing any known conventional $CO_2$ removal systems (114). In one aspect, the removed $CO_2$ can be recycled back to the step of converting at least a portion of the first gas to the synthesis gas comprising $H_2$ and CO. In one exemplary aspect, the removed $CO_2$ can be recycled back to the partial oxidation reactor (116, 118).

The disclosed method can further comprise separating at least a portion of the unreacted synthesis gas from the first product stream utilizing the methane separation unit (120). In the separation step, at least a portion of methane present in the first product stream can be also separated from the first product stream utilizing the methane separation unit (120).

In one aspect, the separation step of at least a portion of the unreacted synthesis gas from the first product stream comprises lowering the pressure of the first product stream, thereby lowering the temperature of the first product stream. In another aspect, the separation step of at least a portion of the unreacted synthesis gas from the first product stream comprises lowering the pressure of the first product stream and the step of using a refrigeration unit, such as a cold box, thereby lowering the temperature of the first product stream. In yet another aspect, the separation step of at least a portion of the unreacted synthesis gas from the first product stream comprises lowering the temperature of the first product stream by the use of a refrigeration unit, such as a cold box.

In one aspect, at least about 80 wt % of the unreacted synthesis gas is separated from the first product stream. In yet another aspect, at least about 90 wt % of the unreacted synthesis gas is separated from the first product stream. In a yet further aspect, at least about 95 wt % of the unreacted synthesis gas is separated from the first product stream. In certain aspects, about 80 wt % to about 99 wt %, such as from about 80 wt % to about 90 wt %, of the unreacted synthesis gas is separated from the first product stream.

In one aspect, at least about 80 wt % of methane is separated from the first product stream. In yet another aspect, at least about 90 wt % of the methane gas is separated from the first product stream. In a yet further aspect, at least about 95 wt % of the methane gas is separated from the first product stream. In certain aspects, about 80 wt % to about 99 wt %, such as from about 80 wt % to about 90 wt %, of methane is separated from the first product stream. In some aspects, at least a portion of the separated methane can be further converted to C2 hydrocarbons. The conversion of the at least a portion of the separated methane can be done utilizing any known in the art conversion methods and conversion catalysts. In certain aspects, at least about 50 wt % of methane is converted to C2 hydrocarbons. In other aspects, at least about 60 wt %, at least about 70 wt %, at least about 80 wt %, at least about 90 wt %, at least about 95 wt % of methane is converted to C2 hydrocarbons. In yet further aspects, about 50 wt % to about 99 wt % of methane is converted to C2 hydrocarbons.

At least a portion of the separated unreacted synthesis gas is further converted to a first alcohol product comprising methanol and C2+ alcohols in alcohol formation and dehydration unit (122). The conversion can be performed utilizing any catalyst known in the art used for the synthesis of methanol. As one of ordinary skill in the art would readily appreciate, C2+ alcohols formed herein comprise a primary alcohol, a secondary alcohol, a tertiary alcohol, or any combination thereof. Suitable catalysts for the conversion of syngas to alcohols is described in Published U.S. application 2014/0135411 to Karim, which is hereby incorporated by reference in its entirety, specifically for its disclosure related to catalysts for alcohol production.

In one aspect, at least about 80 wt % of the unreacted synthesis gas is converted to the first alcohol product. In yet another aspect, at least about 90 wt % of the unreacted synthesis gas is converted to the first alcohol product. In a yet further aspect, at least about 95 wt % of the unreacted synthesis gas is converted to the first alcohol product. In a still further aspect, about 80 wt % to about 99 wt % of the unreacted synthesis gas is converted to the first alcohol product.

In one aspect, at least about 90 wt % of the first alcohol product comprises methanol, ethanol, propanol, butanol, or pentanol, or any combination thereof. In yet another aspect, at least about 95 wt % of the first alcohol product comprises methanol, ethanol, propanol, butanol, or pentanol, or any combination thereof In a yet further aspect, at least about 99 wt % of the first alcohol product comprises methanol, ethanol, propanol, butanol, or pentanol, or any combination thereof. In yet another aspect, the first alcohol product comprises about 90 wt % to about 99 wt % of methanol, ethanol, propanol, butanol, or pentanol, or any combination thereof The disclosed method can further comprise the step of separating at least a portion of C2-C3 hydrocarbons from the first product stream utilizing the C2-C3 separation unit (124). The separation can be done by any separating means known in the art. In one aspect, the at least a portion of C2-C3 hydrocarbons separated from the first product stream comprises olefins and paraffins.

The method described herein further comprises the step of separating at least a portion of the methanol from the first alcohol product using the methanol separation unit (128), thereby producing a second product comprising C2+ alcohols. The second product comprising C2+ alcohols can be further processed. In one aspect, at least a portion of the C2+ alcohols in the second product is dehydrated to C2+ olefins. The dehydration process, for example and without limitation, can comprise an intermolecular dehydration of alcohol with subsequent decomposition of ether. The dehydration process can be done in the presence of any known in the art catalysts. In one aspect, the catalyst used in the dehydration process can comprise an acidic catalyst. For example, the dehydration process can be performed on mesoporous silica catalyst. In another example, the dehydration process can be performed on proton- or metal-modified zeolite catalyst. In yet another example, the dehydration process can be performed on modified alumina or supported heteropolyacids. In one aspect, at least about 80 wt % of C2+ alcohols is dehydrated into C2+ olefins. In another aspect, at least about 90 wt % of C2+ alcohols is dehydrated into C2+ olefins. In yet another aspect, at least about 95 wt % of C2+ alcohols is dehydrated into C2+ olefins. In a yet further aspect, at least about 99 wt % of C2+ alcohols are dehydrated into C2+ olefins. In a further aspect, about 80 wt % to about 99 wt %, such as from about 80 wt % to about 90 wt %, of C2+ alcohols are dehydrated into C2+ olefins.

In one aspect, the C2+ olefins formed in the dehydration step of the at least a portion of C2+ alcohols can be streamed back into the first product stream from the alcohol formation and dehydration unit by fluid communication (126) before the separation step in the C2 and C3 separation unit (124). In this exemplary aspect, the formed C2-C3 olefins are separated together with C2-C3 hydrocarbons originally present in the first product stream from the first product stream utilizing the C2 and C3 separation unit (124). In one aspect, the C2-C3 hydrocarbons originally present in the first product stream can comprise olefins and paraffins. The C2-C3 hydrocarbons originally present in the first product stream together with the formed olefin are provided by fluid communication (130) to the C2-C3 splitters. The method described herein can further comprise the step of separating at least a portion of C2-C3 olefins in the olefin separating unit (134) from the at least a portion of C2-C3 hydrocarbons, thereby producing a third product. In one aspect, at least about 50 wt % of C2-C3 olefins are separated from the at least a portion of C2-C3 hydrocarbons. In another aspect, at least about 70 wt % of C2-C3 olefins are separated from the at least a portion of C2-C3 hydrocarbons. In yet another aspect, at least about 90 wt % of C2-C3 olefins are separated from the at least a portion of C2-C3 hydrocarbons. In a further aspect, at least about 95 wt % of C2-C3 olefins are separated from the at least a portion of C2-C3 hydrocarbons. In a yet further aspect, at least about 99 wt % of C2-C3 olefins are separated from the at least a portion of C2-C3 hydrocarbons. In a further aspect, about 50 wt % to about 99 wt %, such as from 80 wt % to 99 wt %, of C2-C3 olefins are separated from the at least a portion of C2-C3 hydrocarbons.

The separation step can be performed by utilizing the C2-C3 splitters (130). In one aspect the C2 and C3 splitters are deethanizers and depropanizers described herein. In another aspect, the C2-C3 splitters comprise olefin separation columns containing a large number of separation stages. The C2 splitters often can have over 90-100 stage and the C3 splitters can have 150-200 stages. In some aspects, the C2-C3 splitters can comprise fractional trays, random or structured packing. The separated C2-C3 olefins are collected and further utilized in any process that is determined by one of ordinary skill in the art by utilizing any C2-C3 olefin units (134).

In some aspects, to increase production yields and to minimize carbon footprint of the process, at least a portion of the third product formed from the separation of the at least a portion of C2-C3 olefins from the at least a portion of C2-C3 hydrocarbons, can be further recycled into the first gas by fluid communication (132) from the C2-C3 splitters to the partial oxidation reactor.

In certain aspects, at least a portion of methane is left in the first product stream after the methane separation step in the methane separation unit (120). In these aspects, any residual methane can be further converted to C2 hydrocarbons utilizing any methods known in the art.

In some aspects, C4-C9 hydrocarbons and C10+ hydrocarbons originally present in the first product stream along with any residual amounts of methane, the C2 and C3 hydrocarbons that have not been separated from the first product stream during various separation steps can be further processed by utilizing a catalytic convertor in the catalytic conversion unit (136) to form aromatics and C2 and C3 hydrocarbons. In some aspects, the formed aromatics are separated and removed for a further use in the aromatics separation unit (140). In other aspects, the C2 and C3 hydrocarbons formed in this step are recycled by fluid communication (138) to the step of separation of C2 and C3 hydrocarbons from the first product stream into the C2 and C3 separation unit (124). The catalytic convertor can comprise any catalytic convertor known in the art, for example, suitable catalytic converters are, for example, commercially available from KBR and is known as KBR Catalytic Olefin Technology. Steam crackers can also be used, as is known in the art.

In further aspects, all unreacted C10+ hydrocarbons are further separated in the C10+ separation unit (142) and collected to be used for any purpose further determined by one ordinary skill in the art.

In one aspect, the method can produce at least about 50 liters of methanol per hour. In another aspect, the method can produce at least about 100 liters of methanol per hour. In yet another aspect, the method can produce at least about 500 liters of methanol per hour. In yet another aspect, the method can produce at least about 1,000 liters of methanol per hour. For example, the method can produce from about 50 to about 1,000 liters of methanol per hour.

In one aspect, the method can produce at least about 50 liters of C2 and C3 olefins per hour. In another aspect, the method can produce at least about 100 liters of C2 and C3 olefins per hour. In yet another aspect, the method can produce at least about 500 liters of C2 and C3 olefins per hour. In yet another aspect, the method can produce at least about 1,000 liters of C2 and C3 olefins per hour. For example, the method can produce from about 50 to about 1,000 liters of C2 and C3 olefins per hour.

In yet another aspect, the method can produce at least about 50 liters of aromatic hydrocarbons per hour. In a further aspect, the method can produce at least about 100 liters of aromatic hydrocarbons per hour. In yet another aspect, the method can produce at least about 500 liters of aromatic hydrocarbons per hour. In yet another aspect, the method can produce at least about 1,000 liters of aromatic hydrocarbons per hour. For example, the method can produce from about 50 to about 1,000 liters of aromatic hydrocarbons per hour.

In one aspect, the method can produce at least about 50 liters of C10+ hydrocarbons per hour. In another aspect, the method can produce at least about 100 liters of C10+ hydrocarbons per hour. In yet another aspect, the method can produce at least about 500 liters of C10+ hydrocarbons per hour. In yet another aspect, the method can produce at least about 1,000 liters of C10+ hydrocarbons per hour. For example, the method can produce from about 50 to about 1,000 liters of C10+ hydrocarbons per hour.

In some aspects, the method described herein can comprise a) providing natural gas comprising methane, $N_2$, and sulfur; b) removing at least a portion of the sulfur from the natural gas; c) removing at least a portion of the $N_2$ from the natural gas, thereby producing the first gas comprising methane and less than about 1 mole % of $N_2$, d) converting at least a portion of the first gas to synthesis gas comprising $H_2$ and CO, wherein the conversion comprises partially oxidizing the first gas; e) converting at least a portion of the synthesis gas to a first product stream comprising methane, C2-C9 hydrocarbons, C10+ hydrocarbons, aromatics, unreacted synthesis gas, wax, and $CO_2$, wherein the conversion comprises reacting a portion of the $H_2$ and a portion of the CO in synthesis gas in the presence of a Fischer-Tropsch catalyst; f) separating at least a portion of the wax from the first product stream; g) separating at least a portion of the $CO_2$ from the first product stream; h) separating at least a portion of the methane from the first product stream; i) converting at least a portion of the unreacted synthesis gas to the first alcohol product comprising methanol and C2+ alcohols; j) separating at least a portion of the methanol from the first alcohol product, thereby producing the second product; and k) dehydrating the at least a portion of the C2+ alcohols in the second product to C2+ olefins.

In some aspects, the wax, water and/or water vapor can be separated in the wax and water separation unit (112) from the first product stream utilizing any techniques know in the art.

5. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method comprising the steps of: a) providing natural gas comprising methane and $N_2$; b) removing at least a portion of the $N_2$ from the natural gas, thereby producing a first gas comprising methane and less than about 2 mole % of $N_2$; c) converting at least a portion of the first gas to synthesis gas comprising $H_2$ and CO; d) converting at least a portion of the synthesis gas to a first product stream comprising methane, C2-C9 hydrocarbons, C10+ hydrocarbons, unreacted synthesis gas, and $CO_2$; e) separating at least a portion of the unreacted synthesis gas from the first product stream; and f) converting at least a portion of the unreacted synthesis gas to a first alcohol product comprising methanol and C2+ alcohols.

Aspect 2: The method of aspect 1, wherein the first gas comprises less than about 1.5 mole % of $N_2$.

Aspect 3: The method of aspect 1 or 2, wherein the step of converting at least a portion of the first gas to synthesis gas comprising $H_2$ and CO is performed in a partial oxidation reactor.

Aspect 4: The method of any one of aspects 1-3, wherein at least about 80 wt % of the first gas is converted to the synthesis gas comprising $H_2$ and CO.

Aspect 5: The method of any one of aspects 1-4, wherein the first product stream comprises at least about 20 wt % of C2-C5 hydrocarbons.

Aspect 6: The method of any one of aspects 1-4, wherein the first product stream comprises at least about 40 wt % of C2-C5 hydrocarbons.

Aspect 7: The method of any one of aspects 1-4, wherein the first product stream comprises at least about 60 wt % of C2-C5 hydrocarbons.

Aspect 8: The method of any one of aspects 1-4, wherein the first product stream comprises from about 20 wt % to about 70 wt % of C2-C5 hydrocarbons.

Aspect 9: The method of any one of aspects 1-4, wherein the first product stream comprises from about 40 wt % to about 70 wt % of C2-C5 olefins.

Aspect 10: The method of any one of aspects 1-9, wherein the step of separating at least a portion of the unreacted synthesis gas from the first product stream comprises lowering the pressure of the first product stream, thereby lowering the temperature of the first product stream.

Aspect 11: The method of any one of aspects 1-10, wherein at least about 80 wt % of the unreacted synthesis gas is converted to the first alcohol product.

Aspect 12: The method of any one of aspects 1-11, wherein at least about 90 wt % of the first alcohol product comprises methanol, ethanol, propanol, butanol, or pentanol, or any combination thereof Aspect 13: The method of any one of aspects 1-12, wherein the method further comprises the step of separating of at least a portion of $CO_2$ from the first product stream.

Aspect 14: The method of aspect 13, wherein the at least a portion of the separated $CO_2$ is recycled back to the step of converting the at least a portion of the first gas to synthesis gas comprising $H_2$ and CO.

Aspect 15: The method of any one of aspects 1-14, wherein the method further comprises the step of separating at least a portion of C2-C3 hydrocarbons from the first product stream.

Aspect 16: The method of any one of aspects 1-15, wherein the method further comprises the step of separating at least a portion of the methanol from the first alcohol product, thereby producing a second product comprising C2+ alcohols.

Aspect 17: The method of aspect 16, wherein the method further comprises the step of dehydrating at least a portion of the C2+ alcohols in the second product to C2+ olefins.

Aspect 18: The method of any one of aspects 1-17, wherein the natural gas further comprises sulfur and wherein the method further comprises the step of removing at least a portion of the sulfur from the natural gas.

Aspect 19: The method of any one of aspects 14-18, wherein the method further comprises the step of separating at least a portion of C2-C3 olefins from the at least a portion of C2-C3 hydrocarbons, thereby producing a third product.

Aspect 20: The method of aspect 19, wherein at least a portion of the third product is recycled into the first gas.

Aspect 21: The method of any one of aspects 1-20, wherein the method further comprises the step of converting at least a portion of the methane in the first product stream to C2 hydrocarbons.

Aspect 22: The method of any one of aspects 1-21, wherein the method further comprises the step of separating at least a portion of the C10+ hydrocarbons from the first product stream.

Aspect 23: The method of any one of aspects 1-22, wherein the method comprises: a) providing natural gas comprising methane, $N_2$, and sulfur; b) removing at least a portion of the sulfur from the natural gas; c) removing at least a portion of the $N_2$ from the natural gas, thereby producing first gas comprising methane and less than about 1 mole % of $N_2$; d) converting at least a portion of the first gas to synthesis gas comprising $H_2$ and CO, wherein the conversion comprises partially oxidizing the first gas; e) converting at least a portion of the synthesis gas to a first product stream comprising methane, C2-C9 hydrocarbons, C10+ hydrocarbons, aromatics, unreacted synthesis gas, wax, and $CO_2$, wherein the conversion comprises reacting a portion of the $H_2$ and a portion of the CO in synthesis gas in the presence of a Fischer-Tropsch catalyst; f) separating at least a portion of the wax from the first product stream; g) separating at least a portion of the $CO_2$ from the first product stream; h) separating at least a portion of the methane from the first product stream; i) converting at least a portion of the unreacted synthesis gas in the first product stream to a first alcohol product comprising methanol and C2+ alcohols; j) separating at least a portion of the methanol from the first alcohol product, thereby producing a second product; and k) dehydrating the at least a portion of the C2+ alcohols in the second product to C2+ olefins.

Aspect 24: A system comprising: a) a gas expander comprising a first inlet and a first outlet; and an alcohol reactor comprising a second inlet and a second outlet, wherein the gas expander is in fluid communication with the alcohol reactor via a first connector, wherein the first connector is connected to the first outlet of the gas expander and the first inlet of the alcohol reactor.

Aspect 25: The system of aspect 24, wherein the system further comprises a Fischer-Tropsch reactor comprising a third inlet and a third outlet, wherein the Fischer-Tropsch reactor is in fluid communication with the gas expander.

Aspect 26: The system of aspect 25, wherein the system further comprises a partial oxidation reactor comprising a fourth inlet and a fourth outlet, wherein the partial oxidation reactor is in fluid communication with the Fischer-Tropsch reactor.

Aspect 27: The system of aspect 26, wherein the system further comprises an $N_2$ removal unit comprising a fifth inlet and a fifth outlet, wherein the partial oxidation reactor is in fluid communication with the partial oxidation reactor.

Aspect 28: The system of aspect 27, wherein the system further comprises a deethanizer comprising a sixth inlet and a sixth outlet and/or a depropanizer comprising a seventh inlet and a seventh outlet, wherein the gas expander and the alcohol reactor are in fluid communication with the deethanizer and/or depropanizer.

Aspect 29: The system of aspect 28, wherein the system further comprises an olefin separator comprising an eighth inlet and an eight outlet, wherein the olefin separator is in fluid communication with the deethanizer and/or depropanizer.

Aspect 30: The system of any one of aspects 27-29, system further comprises a sulfur removal unit comprising an eleventh inlet and a eleventh outlet, wherein the sulfur removal unit is in fluid communication with the $N_2$ removal unit.

Aspect 31: The system of any one of aspects 24-30, wherein the system is on an industrial scale.

What is claimed is:

1. A method comprising the steps of:
   a) providing natural gas comprising methane and $N_2$;
   b) removing at least a portion of the $N_2$ from the natural gas, thereby producing a first gas comprising methane and less than about 2 mole % of $N_2$;
   c) converting at least a portion of the first gas to synthesis gas comprising $H_2$ and CO;
   d) converting at least a portion of the synthesis gas to a first product stream comprising methane, C2-C9 hydrocarbons, C10+ hydrocarbons, unreacted synthesis gas, and $CO_2$;
   d1) separating at least a portion of the methane from the first product stream:
   e) separating at least a portion of the unreacted synthesis gas from the first product stream; and
   f) converting at least a portion of the unreacted synthesis gas to a first alcohol product comprising methanol and C2+ alcohols.

2. The method of claim 1, wherein the first gas comprises less than about 1.5 mole % of $N_2$.

3. The method of claim 1, wherein the step of converting at least a portion of the first gas to synthesis gas comprising $H_2$ and CO is performed in a partial oxidation reactor.

4. The method of claim 1, wherein at least about 80 wt % of the first gas is converted to the synthesis gas comprising $H_2$ and CO.

5. The method of claim 1, wherein the first product stream comprises at least about 60 wt % of C2-C5 hydrocarbons.

6. The method of claim 1, wherein the first product stream comprises from about 40 wt % to about 70 wt % of C2-C5 olefins.

7. The method of claim 1, wherein the step of separating at least a portion of the unreacted synthesis gas from the first product stream comprises lowering the pressure of the first product stream, thereby lowering the temperature of the first product stream.

8. The method of claim 1, wherein at least about 90 wt % of the first alcohol product comprises methanol, ethanol, propanol, butanol, or pentanol, or any combination thereof.

9. The method of claim 1, wherein the method further comprises the step of separating of at least a portion of $CO_2$ from the first product stream.

10. The method of claim 9, wherein the at least a portion of the separated $CO_2$ is recycled back to the step of converting the at least a portion of the first gas to synthesis gas comprising $H_2$ and CO.

11. The method of claim 1, wherein the method further comprises the step of separating at least a portion of C2-C3 hydrocarbons from the first product stream.

12. The method of claim 1, wherein the method further comprises the step of separating at least a portion of the methanol from the first alcohol product, thereby producing a second product comprising C2+ alcohols.

13. The method of claim 12, wherein the method further comprises the step of dehydrating at least a portion of the C2+ alcohols in the second product to C2+ olefins.

14. The method of claim 1, wherein the natural gas further comprises sulfur and wherein the method further comprises the step of removing at least a portion of the sulfur from the natural gas.

15. The method of claim 11, wherein the method further comprises the step of separating at least a portion of C2-C3 olefins from the at least a portion of C2-C3 hydrocarbons, thereby producing a third product.

16. The method of claim 15, wherein at least a portion of the third product is recycled into the first gas.

17. The method of claim 1, wherein the method further comprises the step of separating at least a portion of the C10+ hydrocarbons from the first product stream.

18. The method of claim 1, wherein the method comprises:
   a) providing natural gas comprising methane, $N_2$, and sulfur;
   b) removing at least a portion of the sulfur from the natural gas;
   c) removing at least a portion of the $N_2$ from the natural gas, thereby producing first gas comprising methane and less than about 1 mole % of $N_2$;
   d) converting at least a portion of the first gas to synthesis gas comprising $H_2$ and CO, wherein the conversion comprises partially oxidizing the first gas;
   e) converting at least a portion of the synthesis gas to a first product stream comprising methane, C2-C9 hydrocarbons, C10+ hydrocarbons, aromatics, unreacted synthesis gas, wax, and $CO_2$, wherein the conversion comprises reacting a portion of the $H_2$ and a portion of the CO in synthesis gas in the presence of a Fischer-Tropsch catalyst;

f) separating at least a portion of the wax from the first product stream;

g) separating at least a portion of the $CO_2$ from the first product stream;

h) separating at least a portion of the methane from the first product stream;

i) converting at least a portion of the unreacted synthesis gas in the first product stream to a first alcohol product comprising methanol and C2+ alcohols;

j) separating at least a portion of the methanol from the first alcohol product, thereby producing a second product; and k) dehydrating the at least a portion of the C2+ alcohols in the second product to C2+ olefins.

* * * * *